United States Patent [19]

Allgeier

[11] Patent Number: 5,098,922

[45] Date of Patent: Mar. 24, 1992

[54] ARALKYL-4H-1,2,4-TRIAZOLE DERIVATIVES

[75] Inventor: Hans Allgeier, Lörrach-Haagen, Fed. Rep. of Germany

[73] Assignee: Ciba-Geigy Corporation, Ardsley, N.Y.

[21] Appl. No.: 718,076

[22] Filed: Jun. 20, 1991

Related U.S. Application Data

[60] Division of Ser. No. 622,130, Dec. 3, 1990, Pat. No. 5,045,556, which is a continuation of Ser. No. 333,378, Apr. 5, 1989, abandoned, which is a continuation-in-part of Ser. No. 290,817, Dec. 22, 1988, abandoned, which is a continuation of Ser. No. 103,147, Oct. 1, 1987, abandoned.

[30] Foreign Application Priority Data

Oct. 9, 1986 [CH] Switzerland ............. 4035/86

[51] Int. Cl.$^5$ ............. A01N 43/653; C07D 249/08
[52] U.S. Cl. ............. 514/383; 548/266.8
[58] Field of Search ............. 548/266.8; 514/383

[56] References Cited

U.S. PATENT DOCUMENTS 4,789,680 12/1988 Meier ............. 514/359

FOREIGN PATENT DOCUMENTS

| | | | |
|---|---|---|---|
| 0126326 | 11/1984 | European Pat. Off. | 548/266.8 |
| 0174562 | 3/1986 | European Pat. Off. | 548/266.8 |
| 0267147 | 5/1988 | European Pat. Off. | 548/266.8 |
| 0206368 | 11/1984 | Japan | 548/266.8 |

OTHER PUBLICATIONS

Pesson, M. "1,2,4-Triazole-5-Carboxylic Amides" CA 70:87820j (1969).
Pesson, M. et al., "1,2,4-Triazole V. N,N-Dialkylamides Derived From 1,2,4-Triazoles-Carboxylic Acids" CA 73:66517n (1970).
Ikizler, A. "Preparation of Some 1,2,4-Trizole Derivatives" CA 99:105183; (1983).
Legraverend, M. "Synthesis of S-Triazolo [4,3rd]-and-[1,5rd]-1,2,4-Triazines" CA 96:217801d (1982).

*Primary Examiner*—C. Warren Ivy
*Assistant Examiner*—Amelia A. Owens
*Attorney, Agent, or Firm*—Irving M. Fishman; Karen G. Kaiser

[57] ABSTRACT

The invention relates to aralkyl-4H-1,2,4-triazole derivatives, especially 5-phenyl-lower alkyl-4H-1,2,4-triazole-3-carboxamides of the formula

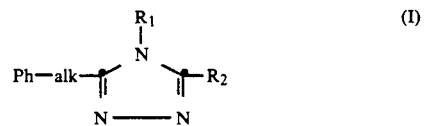

in which Ph represents phenyl substituted by lower alkyl, halogen and/or by trifluoromethyl, alk represents lower alkylidene, $R_1$ is hydrogen or lower alkyl, and $R_2$ represents carbamoyl that is unsubstituted or is substituted by lower alkyl or by lower alkanoyl, and their salts and, as the case may be, their tautomers and the salts thereof. These compounds can be used as pharmaceutical active ingredients.

19 Claims, No Drawings

ARALKYL-4H-1,2,4-TRIAZOLE DERIVATIVES

This is a divisional of Ser. No. 622,130 filed Dec. 3, 1990 now U.S. Pat. No. 5,045,556 which is a continuation of Ser. No. 333,378 filed Apr. 5, 1989 now abandoned which is a continuation-in-part of Ser. No. 290,817 filed Dec. 22, 1988 now abandoned which is a continuation of Ser. No. 103,147 filed Oct. 1, 1987 now abandoned.

The invention relates to novel anti-convulsively active pharmaceutical preparations containing as active ingredient an aralkyl-4H-1,2,4-triazole derivative, especially a 5-phenyl-lower alkyl-4H-1,2,4-triazole-3-carboxamide of the formula

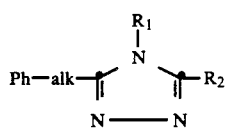   (I)

in which Ph represents phenyl substituted by lower alkyl, halogen and/or by trifluoromethyl, alk represents lower alkylidene, $R_1$ is hydrogen or lower alkyl, and $R_2$ represents carbamoyl that is unsubstituted or is substituted by lower alkyl or by lower alkanoyl, or, as the case may be, a tautomer and/or a pharmaceutically acceptable salt thereof, to the use of said compounds of the formula I, or, as the case may be, their tautomers and/or their pharmaceutically acceptable salts, for the manufacture of anti-convulsively active pharmaceutical preparations, to a method for the treatment of convulsions of various origins, characterised in that one of said compounds of the formula I, or, as the case may be, a tautomer and/or a pharmaceutically acceptable salt thereof, is administered, and to novel 5-phenyl-lower alkyl-4H-1,2,4-triazole-3-carboxamides of the formula I in which Ph represents phenyl substituted by lower alkyl, halogen and/or by trifluoromethyl, alk represents lower alkylidene, $R_1$ is hydrogen or lower alkyl, and $R_2$ represents carbamoyl that is unsubstituted or is substituted by lower alkyl or by lower alkanoyl, with the proviso that, in compounds of the formula I in which $R_1$ represents methyl, $R_2$ represents N,N-diethylcarbamoyl and alk represents methylene, Ph is other than phenyl substituted in the p-position by chlorine, for example those novel 5-phenyl-lower alkyl-4H-1,2,4-triazole-3-carboxamides of the formula I in which Ph is other than phenyl mono-substituted by halogen, especially by chlorine, when $R_2$ represents N,N-di-$C_1$-$C_4$-alkylcarbamoyl in which the two N-alkyl groups are identical or different, and their salts in each case and also, as the case may be, their tautomers in each case and the salts thereof, and to a process for the manufacture of the last-mentioned, novel compounds of the formula I or their tautomers and/or salts.

The phenyl radical Ph contains, for example, up to and including 3, especially 1 or 2, of the mentioned substituents, preferably 1 lower alkyl, trifluoromethyl or halogen substituent or 2 or 3 halogen substituents, or 1 lower alkyl and 1 halogen substituent or 1 trifluoromethyl and 1 halogen substituent, it being preferable for at least one of the lower alkyl and/or halogen substituents to be bonded in an o-position or for a trifluoromethyl radical to be bonded in a m-position. Examples that may be mentioned are: o-halophenyl, m-trifluoromethylphenyl, 2,6- and 2,5-dihalophenyl, or 2,3- and 2,4-dihalophenyl, and o-lower alkylphenyl.

Carbamoyl $R_2$ which is unsubstituted or is substituted by lower alkyl or by lower alkanoyl is, for example, carbamoyl or, secondly, N-lower alkyl-, N,N-di-lower alkyl- or N-lower alkanoyl-carbamoyl.

Tautomeric forms of compounds of the formula I can exist when $R_1$ represents hydrogen. The corresponding 4H-1,2,4-triazole compounds of the formula

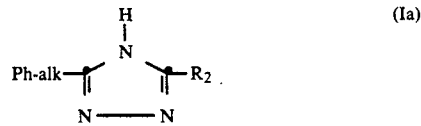   (Ia)

can in that case be in equilibrium with their 1H-1,2,4-triazole tautomers of the formulae

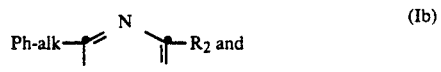   (Ib)

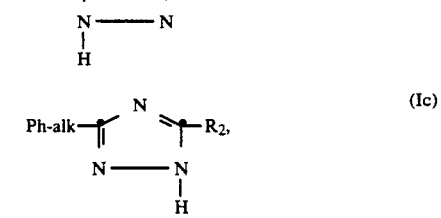   (Ic)

compounds of that type seeming to have predominantly, as far as that is known, the structure Ia.

The compounds of the formula I and, as the case may be, the tautomers thereof may also be in the form of stereoisomers. If, for example, the lower alkylidene group alk or a lower alkyl group (as substituent of Ph or in a substituted carbamoyl group $R_2$) has a chiral carbon atom (C-atom), the compounds of the formula I may be in the form of pure enantiomers or mixtures of enantiomers, such as racemates, or if there is, in addition, at least one further chiral centre within the above-mentioned groups, they may also be in the form of diastereoisomers, mixtures of diastereoisomers or mixtures of racemates.

Salts of compounds of the formula I or, as the case may be, of the tautomers thereof are especially corresponding acid addition salts, preferably pharmaceutically acceptable acid addition salts. These are formed, for example, with strong inorganic acids, such as mineral acids, for example sulphuric acid, a phosphoric acid or a hydrohalic acid, with strong carboxylic acids, such as lower alkanecarboxylic acids, for example acetic acid, optionally unsaturated dicarboxylic acids, for example malonic acid, maleic acid or fumaric acid, or hydroxycarboxylic acids, for example tartaric or citric acid, or with organic sulphonic acids, such as lower alkanesulphonic acids or unsubstituted or substituted benzenesulphonic acids, for example methane- or p-toluene-sulphonic acid. Also included are salts that are unsuitable for pharmaceutical applications, since these can be used, for example, for the isolation and/or purification of free compounds of the formula I and, as the case may be, their tautomers and/or pharmaceutically acceptable salts.

Hereinbefore and hereinafter, unless defined otherwise, organic groups and compounds referred to as "lower" are preferably to be understood as being those containing up to and including 7, especially up to and including 4, C-atoms.

Lower alkyl is, for example, $C_1$–$C_4$-alkyl, such as methyl, ethyl, n-propyl, isopropyl, n-butyl, sec.-butyl, isobutyl or tert.-butyl, but may also be a $C_5$–$C_7$-alkyl group, i.e. a pentyl, hexyl or heptyl group.

Halogen is, for example, halogen having an atomic number of up to and including 35, such as fluorine or chlorine, or secondly bromine.

Lower alkylidene is, for example, $C_1$–$C_4$-alkylidene, especially 1,1-$C_1$–$C_4$-alkylidene, such as methylene or ethylidene, or 1,1-propylidene or 1,1-butylidene, but may also be 2,2-$C_3$–$C_4$-alkylidene, such as 2,2-propylidene (isopropylidene) or 2,2-butylidene.

N-lower alkylcarbamoyl is, for example, N-$C_1$–$C_7$-alkylcarbamoyl, especially N-$C_1$–$C_4$-alkylcarbamoyl, such as N-methyl-, N-ethyl-, N-(n-propyl)-, N-isopropyl-, N-(n-butyl)-, N-isobutyl-, N-sec.-butyl- or N-tert.-butyl-carbamoyl.

N,N-di-lower alkylcarbamoyl is, for example, N,N-di-$C_1$–$C_4$-alkylcarbamoyl, wherein the two N-alkyl groups can in each case be identical or different, such as N,N-dimethyl-, N,N-diethyl-, N,N-diisopropyl- or N-butyl-N-methyl-carbamoyl.

N-lower alkanoylcarbamoyl is, for example, N-$C_2$–$C_7$-alkanoylcarbamoyl, especially N-$C_2$–$C_4$-alkanoylcarbamoyl, such as N-acetyl-, N-propionyl- or N-butyryl-carbamoyl, but may also be N-formylcarbamoyl or N-$C_5$–$C_7$-alkanoylcarbamoyl, such as N-pivaloylcarbamoyl.

The compounds of the formula I and, as the case may be, the tautomers and/or the pharmaceutically acceptable salts thereof have valuable pharmacological properties, especially a pronounced anti-convulsive activity which can be demonstrated, for example, in mice by a marked metrazole antagonism in a dosage range of about 10 mg/kg and above p.o., and in mice and rats by a pronounced protective action against convulsions triggered by electric shock, in a dosage range of about 4 mg/kg and above p.o.. The compounds of the formula I and, as the case may be, the tautomers and/or the pharmaceutically acceptable salts thereof are accordingly outstandingly suitable for the treatment of convulsions of various origins, for example for the treatment of epilepsy. They can accordingly be used as anti-convulsive, for example anti-epileptic, active ingredients in medicaments. The commercial formulation of the active ingredients can also be included.

The invention relates especially to pharmaceutical, especially anti-convulsively active, preparations, to the manufacture thereof and to a method of treatment, characterised in that a compound of the formula I in which Ph represents phenyl mono-, di- or tri-substituted by lower alkyl, halogen and/or by trifluoromethyl, alk represents lower alkylidene, $R_1$ is hydrogen or lower alkyl, and $R_2$ represents carbamoyl, N-lower alkylcarbamoyl, N,N-di-lower alkylcarbamoyl or N-lower alkanoylcarbamoyl, preferably such a compound of the formula I in which Ph carries at least one of the lower alkyl and/or halogen substituents in an o-position or a trifluoromethyl substituent in a m-position, or, as the case may be, a tautomer and/or a pharmaceutically acceptable salt thereof, is selected as active ingredient, and to a compound of the formula I in which Ph represents phenyl mono-, di- or tri-substituted by lower alkyl, halogen and/or by trifluoromethyl, alk represents lower alkylidene, $R_1$ is hydrogen or lower alkyl, and $R_2$ represents carbamoyl, N-lower alkylcarbamoyl, N,N-di-lower alkylcarbamoyl or N-lower alkanoylcarbamoyl, preferably such a compound of the formula I in which Ph carries at least one of the lower alkyl and/or halogen substituents in an o-position or a trifluoromethyl substituent in a m-position, with the proviso that, in a compound of the formula I in which $R_1$ represents methyl, $R_2$ represents N,N-diethylcarbamoyl and alk represents methylene, Ph is other than phenyl substituted in the p-position by chlorine, for example such a compound of the formula I in which Ph is other than phenyl mono-substituted by halogen, especially by chlorine, when $R_2$ represents N,N-di-$C_1$–$C_4$-alkylcarbamoyl in which the two N-alkyl groups are identical or different, and its salts in each case and also, as the case may be, its tautomers in each case and the salts thereof, and to a process for the manufacture of the last-mentioned, novel compounds of the formula I or their tautomers and/or salts.

The invention relates more especially to pharmaceutical, especially anti-convulsively active, preparations, to the manufacture thereof and to a method of treatment, characterised in that a compound of the formula I in which Ph represents phenyl mono-substituted by $C_1$–$C_4$-alkyl, halogen or by trifluoromethyl or di-substituted by halogen, by halogen and $C_1$–$C_4$-alkyl, or by halogen and trifluoromethyl, wherein $C_1$–$C_4$-alkyl in each case represents, for example, methyl and halogen in each case has an atomic number of up to and including 35 and is, independently of any other, for example, fluorine or secondly chlorine, alk represents 1,1- or 2,2-$C_1$–$C_4$-alkylidene, such as methylene or ethylidene, $R_1$ is hydrogen or $C_1$–$C_4$-alkyl, such as methyl or ethyl, and $R_2$ represents carbamoyl, N-$C_1$–$C_4$-alkylcarbamoyl, such as N-methyl- or N-ethyl-carbamoyl, N,N-di-$C_1$–$C_4$-alkylcarbamoyl, such as N,N-dimethylcarbamoyl, or N-$C_2$–$C_7$-alkanoylcarbamoyl, such as N-acetylcarbamoyl, preferably such a compound of the formula I in which Ph carries at least one of the lower alkyl and/or halogen substituents in an o-position or a trifluoromethyl substituent in a m-position, or, as the case may be, a tautomer and/or a pharmaceutically acceptable salt thereof, is selected as active ingredient, and to a compound of the formula I in which Ph represents phenyl mono-substituted by $C_1$–$C_4$-alkyl, halogen or by trifluoromethyl or di-substituted by halogen, by halogen and $C_1$–$C_4$-alkyl, or by halogen and trifluoromethyl, wherein $C_1$–$C_4$-alkyl in each case represents, for example, methyl and halogen in each case has an atomic number of up to and including 35 and is, independently of any other, for example, fluorine or secondly chlorine, alk represents 1,1- or 2,2-$C_1$–$C_4$-alkylidene, such as methylene or ethylidene, $R_1$ is hydrogen or $C_1$–$C_4$-alkyl, such as methyl or ethyl, and $R_2$ represents carbamoyl, N-$C_1$–$C_4$-alkylcarbamoyl, such as N-methyl- or N-ethyl-carbamoyl, N,N-di-$C_1$–$C_4$-alkylcarbamoyl, such as N,N-dimethylcarbamoyl, or N-$C_2$–$C_7$-alkanoylcarbamoyl, such as N-acetylcarbamoyl, preferably such a compound of the formula I in which Ph carries at least one of the lower alkyl and/or halogen substituents in an o-position or a trifluoromethyl substituent in a m-position, with the proviso that, in a compound of the formula I in which $R_1$ represents methyl, $R_2$ represents N,N-diethylcarbamoyl and alk represents methylene, Ph is other than phenyl substituted in the p-position by chlorine, for example such a compound of the formula I in which Ph is other than phenyl mono-substituted by halogen, especially by chlorine, when $R_2$ represents N,N-di-$C_1$–$C_4$-alkylcarbamoyl in which the two N-alkyl groups are identical or different, and in each case its salts and, as the case may be, in each case its tautomers and the salts thereof, and to a process for the manufacture of the last-mentioned, novel compounds of the formula I or their tautomers and/or salts.

The invention relates preferably to pharmaceutical, especially anti-convulsively active, preparations, to the manufacture thereof and to a method of treatment, characterised in that a compound of the formula I in which Ph represents o-$C_1$-$C_4$-alkylphenyl, m-trifluoromethylphenyl, o-halophenyl or 2,5- or 2,6-dihalophenyl, or 2,3- or 2,4-dihalophenyl, wherein $C_1$-$C_4$-alkyl represents, for example, methyl and halogen in each case has an atomic number of up to and including 35 and is, independently of any other, for example, fluorine or secondly chlorine, alk represents 1,1-$C_1$-$C_4$-alkylidene, such as methylene or ethylidene, $R_1$ is hydrogen or $C_1$-$C_4$-alkyl, such as methyl or ethyl, and $R_2$ represents carbamoyl or secondly N-$C_1$-$C_4$-alkylcarbamoyl, such as N-methyl- or N-ethyl-carbamoyl, N,N-di-$C_1$-$C_4$-alkylcarbamoyl, such as N,N-dimethylcarbamoyl, or N-$C_2$-$C_7$-alkanoylcarbamoyl, such as N-acetylcarbamoyl, or, as the case may be, a tautomer and/or a pharmaceutically acceptable salt thereof, is selected as active ingredient, and to a compound of the formula I in which Ph represents o-$C_1$-$C_4$-alkylphenyl, m-trifluoromethylphenyl, o-halophenyl or 2,5- or 2,6-dihalophenyl, or 2,3- or 2,4-dihalophenyl, wherein $C_1$-$C_4$-alkyl represents, for example, methyl and halogen in each case has an atomic number of up to and including 35 and is, independently of any other, for example, fluorine or secondly chlorine, alk represents 1,1-$C_1$-$C_4$-alkylidene, such as methylene or ethylidene, $R_1$ is hydrogen or $C_1$-$C_4$-alkyl, such as methyl or ethyl, and $R_2$ represents carbamoyl or secondly N-$C_1$-$C_4$-alkylcarbamoyl, such as N-methyl- or N-ethyl-carbamoyl, N,N-di-$C_1$-$C_4$-alkylcarbamoyl, such as N,N-dimethylcarbamoyl, or N-$C_2$-$C_7$-alkanoylcarbamoyl, such as N-acetylcarbamoyl, with the proviso that, in a compound of the formula I in which $R_1$ represents methyl, $R_2$ represents N,N-diethylcarbamoyl and alk represents methylene, Ph is other than phenyl substituted in the p-position by chlorine, for example such a compound of the formula I in which Ph is other than phenyl monosubstituted by halogen, especially by chlorine, when $R_2$ represents N,N-di-$C_1$-$C_4$-alkylcarbamoyl in which the two N-alkyl groups are identical or different, and in each case its salts and, as the case may be, in each case its tautomers and the salts thereof, and to a process for the manufacture of the last-mentioned, novel compounds of the formula I or their tautomers and/or salts.

The invention relates especially to pharmaceutical, especially anti-convulsively active, preparations, to the manufacture thereof and to a method of treatment, characterised in that a compound of the formula I in which Ph represents m-trifluoromethylphenyl, o-fluorophenyl or 2,6-difluorophenyl, alk represents methylene, $R_1$ is $C_1$-$C_4$-alkyl, such as methyl or ethyl, and $R_2$ represents carbamoyl, or a pharmaceutically acceptable salt thereof, is selected as active ingredient, and to a compound of the formula I in which Ph represents m-trifluoromethylphenyl, o-fluorophenyl or 2,6-di-fluorophenyl, alk represents methylene, $R_1$ is $C_1$-$C_4$-alkyl, such as methyl or ethyl, and $R_2$ represents carbamoyl, and its salts, and to a process for the manufacture of the last-mentioned, novel compounds of the formula I or their salts.

The invention relates most especially to pharmaceutical, especially anti-convulsively active, preparations, to the manufacture thereof and to a method of treatment, characterised in that a compound of the formula I in which Ph represents m-trifluoromethylphenyl or 2,6-difluorophenyl, alk represents methylene, $R_1$ is $C_1$-$C_4$-alkyl, such as methyl, and $R_2$ represents carbamoyl, or a pharmaceutically acceptable salt thereof, is selected as active ingredient, and to a compound of the formula I in which Ph represents m-trifluoromethylphenyl or 2,6-difluorophenyl, alk represents methylene, $R_1$ is $C_1$-$C_4$-alkyl, such as methyl, and $R_2$ represents carbamoyl, and its salts, and to a process for the manufacture of the last-mentioned, novel compounds of the formula I or their salts.

The invention relates specifically to pharmaceutical, especially anti-convulsively active, preparations, to the manufacture thereof and to a method of treatment, characterised in that one of the novel compounds of the formula I mentioned in the Examples, or, as the case may be, a tautomer and/or a pharmaceutically acceptable salt thereof, is selected as active ingredient, and to the novel compounds of the formula I mentioned in the Examples and their salts and, as the case may be, their tautomers and the salts thereof, and to a process for the manufacture of the last-mentioned, novel compounds of the formula I or their tautomers and/or salts.

The process according to the invention for the manufacture of the novel compounds of the formula I or, as the case may be, their tautomers and/or salts is based on procedures that are known per se. It is characterised, for example, in that a) $X_1$ and $X_2$ are eliminated from a compound of the formula

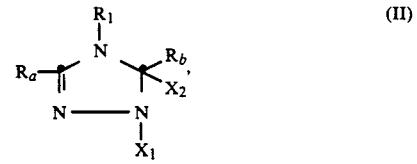

(II)

in which $X_1$ and $X_2$ represent groups that can be eliminated with the formation of an additional bond, and one of the two radicals $R_a$ and $R_b$ is a group Ph-alk and the other is a radical $R_2$, or, as the case may be, from a tautomer and/or salt thereof, or b) in a compound of the formula

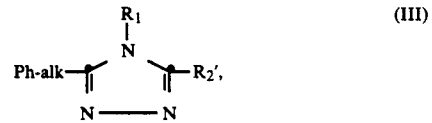

(III)

in which $R_2'$ represents a group that can be converted into a radical $R_2$, or, as the case may be, in a tautomer and/or salt thereof, $R_2'$ is converted into $R_2$, or c) for the manufacture of a compound of the formula I in which $R_1$ is other than hydrogen and $R_2$ is especially N,N-di-lower alkylcarbamoyl, the radical of the formula Ph-alk is introduced into a compound of the formula

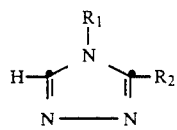
(IV)

or into a salt thereof, or d) for the manufacture of a compound of the formula I in which $R_1$ is hydrogen, in a compound of the formula

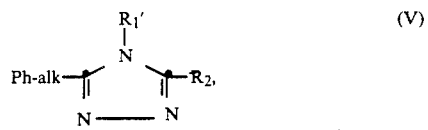
(V)

in which $R_1'$ represents a group that can be replaced by hydrogen, or in a salt thereof, $R_1'$ is replaced by hydrogen, or e) for the manufacture of a compound of the formula I in which $R_2$ is N,N-di-lower alkylcarbamoyl, in a compound of the formula

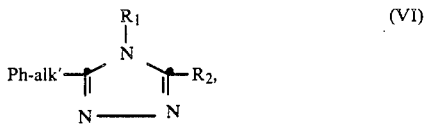
(VI)

in which alk' represents a radical that can be converted into a group alk, or, as the case may be, in a tautomer and/or salt thereof, alk' is converted into alk, and a mixture of isomers which may be obtained in accordance with the process in each variant is separated into its components and the isomer of the formula I is isolated, if desired a compound obtained in each variant in accordance with the process or by other means is converted into a different compound of the formula I, a mixture of stereoisomers which may be obtained in accordance with the process in each variant is separated into the stereoisomers and the desired stereoisomer is isolated, a free compound of the formula I obtained in accordance with the process in each variant is converted into a salt and/or a salt obtained in accordance with the process in each variant is converted into the free compound of the formula I or into a different salt.

The reactions described hereinbefore and hereinafter in the variants and the manufacture of novel starting materials and intermediates are carried out analogously to procedures for the reaction and formation of known starting materials and intermediates. The reactions are carried out, even when this is not expressly mentioned hereinbelow, under the reaction conditions, such as temperature and pressure conditions, that are customary in each case, and using the adjuncts, such as catalysts, condensation agents and solvolysing agents, that are customary in each case, and/or using suitable solvents or diluents or a mixture thereof, and, where appropriate, under a protective gas, in a closed vessel and/or under anhydrous conditions.

In the compounds II that are to be used for process variant a), $X_1$ represents, for example, hydrogen and $X_2$ represents a nucleofugal leaving group. Nucleofugal leaving groups $X_2$ are, for example, optionally etherified or esterified hydroxy or mercapto groups, and also amino, ammonium and sulphonium groups. Etherified hydroxy is, for example, lower alkoxy, such as methoxy or ethoxy, or optionally substituted phenyl-lower alkoxy, such as optionally substituted benzyloxy Esterified hydroxy is especially hydroxy esterified by a mineral acid or an organic sulphonic acid, especially halogen, such as chlorine, bromine or iodine, sulphonyloxy, such as optionally halo-substituted lower alkanesulphonyloxy, for example methanesulphonyloxy or trifluoromethanesulphonyloxy, cycloalkanesulphonyloxy, for example cyclohexanesulphonyloxy, or benzenesulphonyloxy which is optionally substituted by lower alkyl or by halogen, for example benzene-, p-bromophenyl- or p-toluene-sulphonyloxy, or also lower alkanoyloxy, for example acetoxy or pivaloyloxy. Etherified mercapto is, for example, lower alkylthio, such as methylthio or ethylthio, or optionally substituted phenylthio, such as phenylthio or p-tolylthio. Esterified mercapto groups are, for example, lower alkanoylthio groups, such as acetylthio. Amino groups are, for example, amino, N-lower alkylamino, N,N-di-lower alkylamino or N-lower alkanoylamino groups, or also lower alkyleneamino or aza-, oxa- or thia-lower alkyleneamino groups, for example dimethylamino or diethylamino, or pyrrolidino, piperidino, morpholino or thiomorpholino, or also anilino. Ammonium groups are, for example, tertiary or quaternary ammonium groups corresponding to the above-mentioned amino groups, such as tri-lower alkylammonio or pyridinio. Sulphonium groups are, for example, di-lower alkylsulphonium groups, such as dimethylsulphonium.

That which has been said for salts and/or tautomers of compounds I applies analogously to salts and/or tautomers of compounds II.

The elimination of $X_1$ and $X_2$ with the formation of an additional bond (splitting off of $X_1$-$X_2$) is effected in customary manner, for example by heating at from approximately 40° to approximately 200° C., and/or, in the case of compounds II in which $X_2$ represents hydroxy which is optionally esterified by a mineral acid or by an organic sulphonic acid, by treatment with a base, or, in the case of compounds II in which $X_2$ represents optionally etherified hydroxy or mercapto, by treatment with an acid. Bases or acids suitable for this are, for example, the basic or acidic agents, respectively, mentioned hereinafter.

The compounds II are preferably manufactured in situ, for example by cyclising a compound of the formula

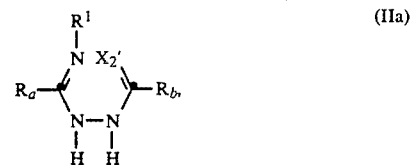
(IIa)

in which $X_2'$ represents optionally functionally modified oxo, or a tautomer and/or salt thereof, the compound II formed as intermediate generally reacting further according to the invention without being isolated.

Optionally functionally modified oxo $X_2'$ is, for example, oxo, thioxo or a group $=N-R_1''$. Groups $=N-R_1''$ are, for example, those in which $R_1''$ represents a group $R_1$ or a group $R_1'$ that can be converted into $R_1$ under the reaction conditions, for example the acyl group, for example imino, N-lower alkylimino, N-lower alkanoylimino or optionally substituted N-benzoylimino.

Tautomers of compounds IIa are, for example, those in which the $R_a$—C(=NR$_1$)—NH grouping is in protomeric form, i.e. in the form of the $R_a$—C(NHR$_1$)=N grouping. It is also possible, for example, for a compound IIa containing an oxo, thioxo or imino group $X_2'$ to be in its tautomeric form as an enol, en-thiol or en-amine of the formula

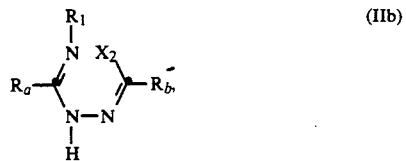

in which $X_2$ represents hydroxy, mercapto or amino

That which has been said for salts of compounds I applies analogously to salts of compounds IIa or IIb.

The cyclisation of compounds IIa or their tautomers and/or salts and, where appropriate, the subsequent in situ elimination of $X_1$-$X_2$ from the resulting compounds II or, as the case may be, their tautomers and/or salts are effected in customary manner, i.e. under neutral, acidic or basic conditions, if necessary in the presence of an acidic or basic agent, in the presence of an inert solvent or diluent or a mixture thereof, at room temperature or, preferably, while heating, for example in a temperature range of from approximately 40° to approximately 200° C., preferably from approximately 60° to approximately 140° C., and/or under an inert gas, such as nitrogen.

Suitable acidic agents are, for example, mineral acids or their anhydrides or acid salts, for example hydrohalic acids, sulphuric acid, alkali metal hydrogen sulphates, phosphoric acid, polyphosphoric acid, phosphorus pentoxide, phosphorus trichloride, phosphorus oxychloride or phosphorus tribromide, organic sulphonic acids, such as p-toluenesulphonic acid, or carboxylic acids or their anhydrides or halides, such as lower alkanoic acids or their anhydrides or halides, for example acetic acid, acetic anhydride or acetyl chloride, or buffered acid solutions, for example phosphate or acetate buffer, or hydrohalides of nitrogen bases, for example ammonium chloride or pyridinium chloride.

Basic agents are, for example, hydroxides, hydrides, amides, lower alkoxides, carbonates, di-lower alkylamides or lower alkylsilylamides of alkali metals or alkaline earth metals, lower alkylamines, basic heterocycles, ammonium hydroxides and carbocyclic amines. Examples that may be mentioned are sodium hydroxide, hydride, amide, methoxide, ethoxide or carbonate, potassium hydroxide, tert.-butoxide or carbonate, lithium diisopropylamide, potassium bis-(trimethylsilyl)-amide, calcium hydroxide or hydride, di- or tri-ethylamine, pyridine, benzyltrimethylammonium hydroxide, 1,5-diazabicyclo[4.3.0]-non-5-ene (DBN) and 1,5-diazabicyclo[5.4.0]undec-5-ene (DBU).

Inert solvents or diluents that may be mentioned are, for example, halo-lower alkanes, cyclic ethers, aromatic hydrocarbons, N,N-di-lower alkyl-lower alkanoic acid amides, phosphoric acid lower alkylamides, di-lower alkyl sulphoxides and cyclic amines, and also, especially when carrying out the reaction in the presence of an alcoholate, the alcohols corresponding to the alcoholate: for example di-, tri- or tetrachloromethane, tetrahydrofuran, dioxan, benzene, toluene, xylene, N,N-dimethylformamide, hexamethylphosphoric acid triamide, dimethyl sulphoxide or N-methylmorpholine, and also, for example, methanol, ethanol or tert.-butanol.

The compounds IIa or their tautomers and/or salts can be manufactured, for example, by reacting with each other corresponding compounds of the formulae

in which $Z_1$ represents a nucleofugal leaving group $X_2$, $X_2'$ represents optionally functionally modified oxo, and $Z_2$ represents hydrazino, or tautomers and/or salts thereof, and can advantageously be reacted further in situ to form compounds II and I.

For example, compounds IIa in which $R_a$ is a group Ph-alk, $R_b$ is a radical $R_2$ and $X_2'$ is optionally functionally modified oxo, preferably oxo, are preferably obtained by reacting with each other corresponding compounds of the formulae IIc and IId in which $Z_1$ represents a nucleofugal leaving group $X_2$, preferably lower alkoxy, $X_2'$ represents optionally functionally modified oxo, preferably oxo, and $Z_2$ represents hydrazino, or, as the case may be, their tautomers and/or salts, the reaction preferably being carried out in one of the inert solvents described hereinbefore, while heating, for example in a temperature range of from approximately 20° to approximately 200° C., especially from approximately 40° to approximately 140° C., optionally in the presence of one of the acidic or basic agents mentioned above and/or under an inert gas, such as nitrogen. The compounds IIc ($R_a$=Ph-alk, $Z_1$=lower alkoxy) are obtained, for example, by reacting a phenylalkanoic acid amide of the formula Ph-alk-CONHR$_1$ (IIe) with a suitable lower alkylating agent, preferably a tri-lower alkyloxonium tetrafluoroborate, such as triethyloxonium tetrafluoroborate, for example in dichloromethane, or by reacting a nitrile of the formula Ph-alk-CN (IIf) with an alcohol in the presence of dry hydrogen chloride gas and optionally converting the resulting iminium hydrochloride into the free base by treatment with a weak base, such as sodium hydrogen carbonate. The compounds IId ($R_b$=R$_2$, $X_2'$=oxo, $Z_2$=hydrazino) are known or can be manufactured analogously to known methods.

Analogously, compounds IIa in which $R_a$ is a group $R_2$, $R_b$ is a radical Ph-alk and $X_2'$ is optionally functionally modified oxo, preferably oxo, can be obtained preferably by reacting with each other corresponding compounds IIc and IId in which $Z_1$ represents a nucleofugal leaving group $X_2$, preferably halogen, such as chlorine, $X_2'$ represents optionally functionally modified oxo, preferably oxo, and $Z_2$ represents hydrazino, or, as the case may be, their tautomers and/or salts, the reaction preferably being carried out, for example, while cooling, for example in a temperature range of from approximately $-20°$ to approximately $+15°$ C., especially from approximately $-5°$ to approximately $+10°$ C., in an inert solvent, in the presence of a basic agent and/or under an inert gas, such as nitrogen. The compounds IIc ($R_a=R_2$, $Z_1$=halogen) are known or can be obtained analogously to known methods, for example by reacting optionally N-lower alkyl-, N,N-di-lower alkyl- or N-lower alkanoyl-substituted oxalic acid diamides with halogenating agents, such as phosgene or phosphorus tribromide. The compounds IId ($R_b$=Ph-alk, $X_2'$=oxo, $Z_2$=hydrazino) are known or can be manufactured analogously to known methods.

Compounds IIa in which $R_a$ is a group $R_2$, $R_b$ is a radical Ph-alk and $X_2'$ is optionally functionally modified oxo, preferably oxo, can also be obtained by first reacting with each other a compound of the formula $R_1N=C(Z_1)$-$R_2'$ (IIc') in which $R_2'$ is, for example, lower alkoxycarbonyl, such as ethoxycarbonyl, or optionally substituted phenyl-lower alkoxycarbonyl, and $Z_1$ is a nucleofugal leaving group $X_2$, preferably halogen, such as chlorine, and a compound IId in which $R_b$ represents a radical Ph-alk, $X_2'$ represents optionally functionally modified oxo, preferably oxo, and $Z_2$ represents hydrazino, or, as the case may be, a tautomer and/or salt thereof in each case, for example under the reaction conditions indicated above, for example while cooling and/or in the presence of a basic agent, and then, in the resulting compound of the formula $R_2'C(=NR_1)$-NHNH-$C(=X_2')$alk-Ph (IIa'), or in a tautomer and/or salt thereof which may be obtained, solvolysing the group $R_2'$ to a carbamoyl group $R_2$, for example by reaction with ammonia, N-mono- or N,N-di-lower alkylamines or N-lower alkanoylamines, advantageously while heating, for example in a temperature range of from approximately 30° to approximately 100° C., preferably from approximately 40° to approximately 80° C., in the presence of an agent that removes the elements of water, such as N,N'-dicyclohexylcarbodiimide, and/or under an inert gas, such as nitrogen. The compounds IIc' are known or can be obtained analogously to that described above by reacting oxalic acid monoalkyl ester monoamides with halogenating agents, such as phosgene or phosphorus tribromide.

Analogously, compounds IIa in which $R_a$ is a group Ph-alk, $R_b$ is a radical $R_2$ and $X_2'$ is optionally functionally modified oxo, preferably oxo, can also be obtained by first reacting with each other a compound of the formula $H_2N$-NH-$C(=X_2')$-$R_2'$ (IId') in which $R_2'$ is, for example, lower alkoxycarbonyl, such as ethoxycarbonyl, or optionally substituted phenyl-lower alkoxycarbonyl and $X_2'$ is optionally functionally modified oxo, preferably oxo, and a compound IIc in which $R_a$ is a radical Ph-alk and $Z_1$ is a nucleofugal leaving group $X_2$, preferably lower alkoxy, or, as the case may be, a tautomer and/or salt thereof in each case, for example under the reaction conditions indicated above, for example while cooling and/or in the presence of a basic agent, and then, in the resulting compound of the formula Ph-alk—$C(=NR_1)$—NHNH—$C(=X_2')$—$R_2'$ (IIa"), or in a tautomer and/or salt thereof which may be obtained, solvolysing the group $R_2'$ to a carbamoyl group $R_2$, for example by reaction with ammonia, N-mono- or N,N-di-lower alkylamines or N-lower alkanoylamines under the reaction conditions described hereinbefore. The compounds IId' are known or can be obtained analogously to known methods.

Compounds IIa in which one of the two radicals $R_a$ and $R_b$ represents a group Ph-alk and the other represents a radical $R_2$ and $X_2'$is optionally functionally modified oxo, preferably oxo, can also be obtained by reacting a compound of the formula Ph-alk—$C(=X_2')$NHNHC$(=X_2'')$—$Z_3$ (IIg) in which each of $X_2'$ and $X_2''$, independently of the other, represents optionally functionally modified oxo, preferably both oxo, and $Z_3$ represents either a radical $R_2$ or a group $R_2'$ that can be converted into a radical $R_2$, preferably a lower alkoxycarbonyl group, such as an ethoxycarbonyl group, or an optionally substituted phenyl-lower alkoxycarbonyl group, or, as the case may be, a tautomer and/or salt thereof, with ammonia or with an amine $R_1NH_2$, advantageously in the presence of a basic agent, such as pyridine, and, where appropriate, subsequently converting a group $R_2'$ into the radical $R_2$, for example by solvolysis, for example by reaction with ammonia, N-mono- or N,N-di-lower alkylamines or N-lower alkanoylamines under the reaction conditions described above. The compounds IIg can be obtained analogously to known methods, for example by reacting a compound of the formula $Z_3$—$C(=X_2'')$—$NHNH_2$ (IId") with a compound of the formula Ph-alk—$C(=X_2')$-$Z_1$ (IIc") in which $Z_1$ represents a nucleofugal leaving group $X_2$, preferably lower alkoxy.

In an especially preferred form of process variant a), a compound IIc ($R_a$=Ph-alk, $Z_1$=lower alkoxy) is first reacted at from approximately 80° to approximately 120° C., for example in N-methylmorpholine or N,N-dimethylformamide, with a compound IId ($R_b=R_2$, $X_2'$=oxo, $Z_2$=hydrazino), the initially formed product IIa ($R_a$=Ph-alk, $R_b=R_2$, $X_2'$=oxo) then reacting further in situ to form first the corresponding compound II ($R_a$=Ph-alk, $R_b=R_2$, $X_1$=hydrogen, $X_2$=hydroxy) as intermediate, and then, by in-situ-elimination of the elements of water, to yield the corresponding compound of the formula I as end product.

Groups $R_2'$ that can be converted according to process variant b) into optionally N-mono- or N,N-di-lower alkylated or N-lower alkanoylated carbamoyl radicals $R_2$ are either groups $R_2'$ that can be solvolysed to radicals $R_2$ or groups $R_2'$ that can be converted into radicals $R_2$ by oxidation. Groups $R_2'$ that can be solvolysed to radicals $R_2$ are preferably, for example, free or esterified carboxy groups or carboxy groups in the form of a salt or an anhydride, the cyano group or optionally lower alkylated or lower alkanoylated amidino groups.

Esterified carboxy groups are, for example, carboxy groups esterified by a lower alkanol or a lower alkyl mercaptan, i.e. lower alkoxycarbonyl or lower alkylthiocarbonyl groups, but may also be esterified by another alcohol or mercaptan, for example by an optionally substituted phenol.

Carboxy groups in the form of salts are, for example, carboxy groups in the form of an ammonium salt derived from ammonia or a mono- or di-lower alkylamine, or carboxy groups in the form of a metal salt, for example in the form of an alkali metal salt or an alkaline earth metal salt.

Carboxy groups in the form of an anhydride are, for example, carboxy groups in the form of a halide, such as chlorocarbonyl, but may also be anhydridised with a reactive carboxylic acid and be, for example, alkoxycarbonyloxycarbonyl or trifluoroacetoxycarbonyl.

Optionally lower alkylated or lower alkanoylated amidino groups are, for example, unsubstituted or N-lower alkylated, N,N-di-lower alkylated or N-lower alkanoylated amidino groups.

That which has been said above for salts and/or tautomers of compounds I applies analogously to salts and/or tautomers of compounds III.

The conversion of the mentioned groups $R_2'$ into carbamoyl that is unsubstituted or substituted as stated is effected in customary manner, for example by solvolysis, that is to say hydrolysis, ammonolysis or aminolysis (reaction with water or ammonia or a mono- or di-lower alkylamine).

By hydrolysis it is possible to convert, for example, unsubstituted or N-mono- or N,N-di-lower alkylated or N-lower alkanoylated amidino groups $R_2'$ into optionally lower alkylated or lower alkanoylated carbamoyl groups, or to convert cyano $R_2'$ into carbamoyl. The hydrolysis of the mentioned amidino groups is effected, for example, under acidic conditions, for example in the presence of mineral acids, for example hydrochloric or sulphuric acid. The hydrolysis of cyano is carried out, for example, in the presence of a basic hydrolysing agent, such as an alkali metal hydroxide, for example sodium hydroxide solution or potassium hydroxide solution It can be facilitated by peroxy compounds, for example hydrogen peroxide, and is effected, for example, in a lower alkanol, for example in ethanol, as diluent.

By ammonolysis or aminolysis it is possible to convert, for example, free or esterified carboxy groups $R_2'$ or carboxy groups $R_2'$ in the form of a salt or an anhydride into unsubstituted or lower-alkylated carbamoyl. If necessary, the operation is carried out in the presence of a condensation agent, advantageously in an inert solvent. Condensation agents are, for example, basic condensation agents, especially ammonia or amines used for the aminolysis in excess and, when starting from carboxy in the form of an anhydride, also alkali metal hydroxides or carbonates, or tertiary organic nitrogen bases, such as tri-lower alkylamines or tertiary heteroaromatic nitrogen bases, for example triethylamine or pyridine. An especially suitable inert solvent is, for example, toluene and, in the solvolysis of esterified carboxy groups, also ethanol. Free carboxy groups can be converted into optionally lower alkylated carbamoyl by removing the elements of water from the ammonium salts formed as intermediates, for example by heating or by the action of dehydrating agents, such as by the action of acid anhydrides, for example phosphorus pentoxide, acetyl chloride and the like, or of carbodiimides, for example N,N'-dicyclohexylcarbodiimide.

As a group $R_2'$ that can be converted by oxidation into a carbamoyl group $R_2$ which is unsubstituted or substituted as indicated there comes into consideration, for example, the formyl group. The conversion thereof by oxidation is carried out according to customary methods. For example, the aldehydes of the formula

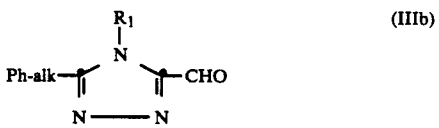

(IIIb)

can be converted into corresponding compounds I by treatment with ammonia or an N-mono- or N,N-di-lower alkylamine under oxidising conditions, for example in the presence of oxidising heavy metal compounds, such as manganese(IV), iron(VI) or nickel(IV) compounds or heavy metal peroxides, for example nickel peroxide. In this conversion, the compounds IIIb are treated, for example, with dry ammonia gas while cooling, for example in a temperature range of from approximately $-60°$ to approximately $\pm 0°$ C., especially from approximately $-30°$ to approximately $-15°$ C., and in the presence of nickel peroxide, or the aldehyde IIIb is reacted with manganese dioxide and sodium cyanide in the presence of ammonia or an N-lower alkyl- or N,N-di-lower alkyl-amine, the reaction being carried out, for example, in isopropanol as solvent and while cooling, for example in a temperature range of from approximately $-20°$ to approximately $+10°$ C., especially from approximately $-5°$ to approximately $+5°$ C.

The starting materials of the formula III in which $R_2'$ represents one of the described radicals that can be converted into $R_2$ can be obtained by several methods, for example by eliminating $X_1$ and $X_2$, for example in a manner analogous to that described in process variant a), from a compound of the formula

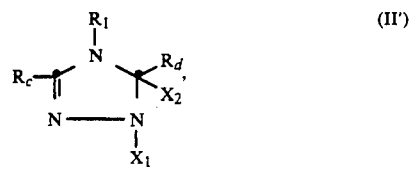

(II')

in which $X_1$ and $X_2$ represent groups that can be eliminated with the formation of an additional bond and one of the radicals $R_c$ and $R_d$ represents a group Ph-alk and the other represents a radical $R_2'$, or, as the case may be, from a tautomer and/or salt thereof The compounds II' are preferably manufactured in situ, for example by cyclising a compound of the formula

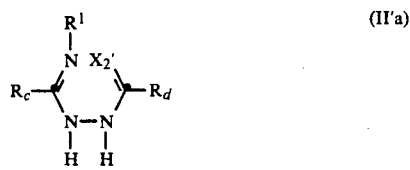

(II'a)

in which $X_2'$ represents optionally functionally modified oxo, or a tautomer and/or salt thereof, the cyclisation being carried out in a manner analogous to that described in process variant a). The compounds II'a can be manufactured, for example, in a manner analogous to that described in process variant a) for compounds IIa' or IIa".

A further method of manufacturing the starting materials of the formula III in which $R_2'$ represents one of the described radicals that can be solvolysed to $R_2$ is based on the introduction of the radical Ph-alk into a compound of the formula

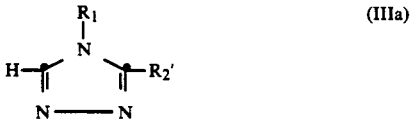

(IIIa)

or into a salt thereof, the operation being carried out in a manner analogous to that described in process variant c).

Compounds III which are obtainable in accordance with the process and in which $R_2'$ represents esterified carboxy or cyano can subsequently be hydrolysed, for example by treatment with sodium hydroxide or potassium hydroxide in aqueous-ethanolic solution, to form the corresponding carboxylic acids (III; $R_2'$=carboxy) which, in a further reaction step, can be converted into the acid chlorides (III; $R_2'$=chlorocarbonyl), for example by means of thionyl chloride in toluene/pyridine or phosphorus pentachloride in tetrahydrofuran or by means of phosphorus oxychloride. Nitriles (III; $R_2'$=cyano) formed initially can also be converted by reaction with a mineral acid, for example with hydrochloric or hydrobromic acid or sulphuric acid, and an alcohol, for example a lower alkanol or benzyl alcohol, and further reaction of the resulting imino ether with ammonia or a mono- or di-lower alkylamine, into the corresponding amidines (III; $R_2'$=optionally lower alkylated amidino).

In a preferred embodiment for the manufacture of compounds III in which $R_2'$ is esterified carboxy, compounds of the formulae

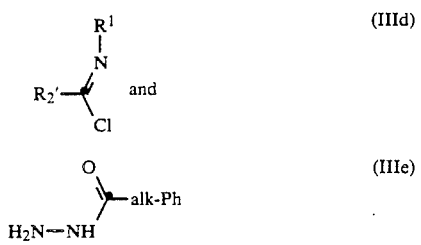

are reacted with each other in toluene and the resulting initial product IIa' ($X_2'$=oxo) is converted in situ, without additional purification, by heating for several hours in boiling xylene, into the corresponding intermediate compound II' ($R_c$=esterified carboxy $R_2'$, $R_d$=Ph-alk, $X_1$=hydrogen, $X_2$=hydroxy), and then, by in-situ-elimination of the elements of water, into the desired intermediate III ($R_2'$=esterified carboxy)

Starting materials III in which $R_2'$ represents formyl, i.e. aldehydes IIIb, are also obtainable by oxidation of corresponding primary alcohols of the formula III ($R_2'$=hydroxymethyl), the reaction being carried out under the customary reaction conditions and using oxidation systems that are customary for that purpose, such as dimethyl sulphoxide/oxalyl chloride, chromium trioxide, sodium dichromate/water, pyridinium chlorochromate, potassium permanganate, manganese dioxide, bismuth trioxide, nickel peroxide, ceric ammonium nitrate, lead tetraacetate/pyridine or N-chlorosuccinimide, or using oxygen, for example in the presence of suitable catalysts, such as metal oxides, for example aluminium oxide, silicon dioxide or iron(III) oxide, or by means of dehydrogenating catalysts, such as copper oxide or copper chromite. If nickel peroxide or manganese dioxide are used as oxidising agents, the aldehyde stage does not need to be isolated but can be further reacted in situ with ammonia or the corresponding amine. The corresponding primary alcohols (III; $R_2'$=hydroxymethyl) can be obtained, for example, by reaction of triazoles of the formula

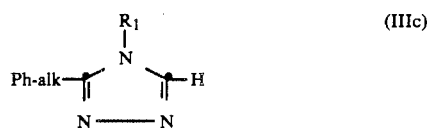

with formaldehyde or formaldehyde equivalents, such as paraformaldehyde, in the presence of a basic agent. Suitable basic agents are especially organometal bases, such as alkali metal lower alkyl or alkali metal phenyl compounds, for example methyl- or butyl-lithium or phenyl sodium, which are used while cooling, for example in a temperature range of from approximately $-100°$ to approximately $+10°$ C., especially from approximately $-80°$ to approximately $-20°$ C., under an inert gas, such as nitrogen, and/or in the presence of an inert solvent, such as tetrahydrofuran or 1,2-dimethoxyethane. In a preferred embodiment, gaseous formaldehyde is introduced into the basic reaction mixture. The primary alcohols (III; $R_2'$=hydroxymethyl) can also be manufactured from corresponding compounds II'.

In an alternative procedure, the triazole IIIc can be deprotonated as described and converted by reaction with N,N-di-lower alkylformamides, for example N,N-dimethylformamide, directly into the aldehyde of the formula IIIb.

The triazoles IIIc can be manufactured, for example, by reacting a compound of the formula $HalC(=NR_1)H$ (IIIf) in which Hal represents halogen, such as chlorine, in a manner analogous to that described for compounds IIc in process variant a), with a compound IId ($R_b$=Ph-alk, $X_2'$=oxo, $Z_2$=hydrazino).

The introduction of the radical of the formula Ph-alk into a compound of the formula IV (to the salts of which there applies analogously that which has been said above for salts of compounds I) in accordance with process variant c) is effected, for example, by reaction with a reactive ester of a corresponding phenyl-lower alkanol that is substituted in the phenyl moiety.

Reactive esters of phenyl-lower alkanols that are substituted in the phenyl moiety have, for example, the formula Ph-alk-$Z_4$ (IVa), there coming into consideration as reactive esterified hydroxy $Z_4$ preferably hydroxy esterified by a mineral acid or by an organic sulphonic acid, such as hydroxy esterified by a hydrohalic acid or by an aliphatic or aromatic sulphonic acid, for example chlorine, bromine or iodine or methane-, ethane-, benzene- or p-toluene-sulphonyloxy.

The reaction is carried out, for example, under basic conditions, such as in the presence of a basic condensation agent, for example of the kind indicated in process variant a), preferably in one of the solvents or diluents that are also indicated there, if necessary while heating and/or under an inert gas, such as nitrogen.

The compounds of the formula IV are known or can be manufactured analogously to known methods, for example by reacting formylhydrazine with a compound IIc in which $R_a$ represents a radical $R_2$ and $Z_1$ represents a nucleofugal leaving group $X_2$, preferably halogen, such as chlorine, the customary reaction conditions, for example as described in process variant a), being applied.

Groups $R_1'$ that are replaceable by hydrogen in accordance with process variant d) are, for example, acyl groups, for example acyl groups derived from an organic carboxylic or sulphonic acid.

Acyl derived from an organic carboxylic acid is, for example, the radical of an aliphatic or monocyclic aromatic carboxylic acid, such as lower alkanoyl or optionally substituted benzoyl, also pyridoyl. Acyl derived from an organic sulphonic acid is, for example, lower alkanesulphonyl.

That which has been said for salts of compounds I applies analogously to salts of compounds V.

For the exchange of the acyl group $R_1'$ for hydrogen there come into consideration the customary reduction systems and reaction conditions, for example diborane, lithium aluminium hydride, sodium borohydride/cobalt(II) chloride, sodium borohydride/-trifluoroacetic acid or trihalosilanes, for example trichlorosilane.

The starting materials V can be obtained, for example, analogously to the elimination methods described in process variant a). For example, a compound of the formula

(Va)

in which $X_2'''$ represents a group $=N-R_1'$ ($R_1'=$acyl) and $Z_1$ represents a nucleofugal leaving group $X_2$, for example as described in process variant a), and a compound IId in which $R_b$ represents a radical $R_2$, $X_2'$ represents optionally functionally modified oxo, preferably oxo, and $Z_2$ represents hydrazino, or, as the case may be, a tautomer and/or salt thereof in each case, can be reacted with each other, the initially formed product of the formula $Ph\text{-alk}-C(=NR_1')-NHNHC(=O)R_2$ (Vb) then reacting further in situ to form first an intermediate of the formula

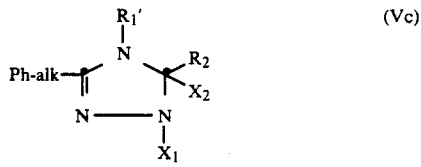

(Vc)

in which $X_1$ represents hydrogen and $X_2$ represents hydroxy, and then, by in-situ-elimination of the elements of water, to yield the corresponding compound of the formula V as end product.

The starting materials of the formula Va can be obtained, for example, by reacting correspondingly N-substituted phenylalkanoic acid amides of the formula Ph-alk—C(=O)NHR$_1'$ (Vd) with a tri-lower alkyloxonium tetrafluoroborate, such as triethyloxonium tetrafluoroborate, analogously to the procedure described in process variant a).

In the compounds of the formula VI which are to be used in accordance with process variant e) (to the salts and/or tautomers of which there applies analogously that which has been said above for salts and/or tautomers of compounds I), a radical alk' that can be converted into a group alk is especially an α-hydroxy-lower alkylidene radical -alk''(OH)- in which alk'' represents a lower alkylidene group that can have the meanings defined for the group alk in the compounds of the formula I, and, in addition, is substituted by hydroxy at the C-atom linking the two ring systems. The corresponding compounds of the formula

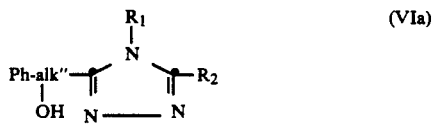

(VIa)

in which $R_2$ represents N,N-di-lower alkylcarbamoyl, such as N,N-dimethylcarbamoyl, are reduced to compounds of the formula I according to the invention by reduction of the hydroxy-lower alkylidene group. The customary reaction conditions and reduction systems are used for the reduction, for example copper chromite, palladiumon-carbon, lithium aluminium hydride/aluminium chloride, iodine/water/red phosphorus or hydrogen in the presence of catalysts, such as platinum. Two-stage reduction methods also are customary, for example conversion of the alcohol into a sulphonate, for example p-toluenesulphonate, and reduction of the sulphonate in situ, for example with lithium aluminium hydride in tetrahydrofuran.

The starting materials VIa are obtained, for example, by reacting a compound IV in which $R_2$ represents N,N-di-lower alkylcarbamoyl, such as N,N-dimethylcarbamoyl, in the presence of a basic agent, for example of the kind indicated in process variant a), with an aldehyde of the formula Ph-CHO (VIb), the customary reaction parameters being chosen.

Compounds of the formula I obtainable in accordance with the process or by other means can be converted into other compounds of the formula I by converting one or more variables of the general formula I into other variables.

For example, in compounds I, unsubstituted carbamoyl $R_2$ can be converted into N-mono- or N,N-di-lower alkylcarbamoyl, and N-mono-lower alkylcarbamoyl $R_2$ can be converted into N,N-di-lower alkylcarbamoyl, for example by treatment with a reactive ester of a lower alkanol, such as a lower alkyl halide, for example bromide or iodide, lower alkylsulphonate, for example methanesulphonate or p-toluenesulphonate, or a di-lower alkyl sulphate, for example dimethyl sulphate, preferably under basic conditions, such as in the presence of sodium hydride or in the presence of sodium hydroxide solution or potassium hydroxide solution and a phase-transfer catalyst, such as tetrabutylammonium bromide or benzyltrimethylammonium chloride.

Similarly, compounds I in which $R_1$ represents hydrogen can be N-lower alkylated in analogous manner to compounds I in which $R_1$ represents lower alkyl. The N-alkylation can also be carried out in such a manner that when compounds I in which $R_1$ represents hydrogen and $R_2$ represents unsubstituted carbamoyl are used as starting material, under the corresponding reaction conditions, in addition to the introduction of the N-lower alkyl group $R_1$, N-alkylation to N-mono- or N,N-di-lower alkylcarbamoyl $R_2$ also is achieved in the same reaction step. It is possible to proceed analogously when compounds I in which $R_1$ represents hydrogen and $R_2$ is N-mono-lower alkyl-substituted carbamoyl are used as starting material. According to that method of N-alkylation, compounds I in which all of the N-lower alkyl groups introduced in the same reaction step are of the same type are obtained in each case.

It is also possible to convert unsubstituted carbamoyl $R_2$ into N-lower alkanoylcarbamoyl, for example by reaction with a lower alkanoic acid, such as formic, acetic or propionic acid, or a derivative of such an acid, for example an acid halide, such as an acid chloride, an ester or especially an anhydride, for example acetyl chloride or acetic anhydride, but it may be necessary to use more strongly basic condensation agents, such as alkali metal amides or alkali metal alcoholates, for example sodium amide or sodium methoxide, or alternatively acid condensation agents, such as mineral acids, for example sulphuric acid. Compounds in which $R_1$ is hydrogen are also N-lower alkanoylated at the $N^4$ atom during the reaction, so that, when the reaction is complete, the lower alkanoyl group must be removed from the $N^4$ atom in an additional step, for example as described under process variant d).

Salts of compounds of the formula I, or, as the case may be, of their tautomers, can be manufactured in a manner known per se. For example, acid addition salts of compounds of the formula I are obtained by treatment with an acid or a suitable ion-exchange reagent. The acid addition salts can be converted into the free compounds in customary manner, for example by treatment with a suitable basic agent.

Depending on the procedure and reaction conditions, the compounds of the formula I having salt-forming, especially basic, properties, or, as the case may be, tautomers thereof, may be obtained in free form or in the form of salts.

Owing to the close relationship between the compounds of the formula I in free form and in the form of their salts, hereinbefore and hereinafter there is to be understood by the free compounds or their salts, where appropriate and expedient, also the corresponding salts or the free compounds, respectively.

The novel compounds of the formula I including their salts in the case of salt-forming compounds can also be obtained in the form of their hydrates or can include other solvents, for example solvents used for crystallisation of compounds that are in solid form.

Depending on the starting materials and procedures chosen, the novel compounds of the formula I may be in the form of one of the possible isomers or in the form of a mixture thereof. Depending on the symmetry of the molecule, for example depending on the number and absolute and relative configuration of the chiral centres, such as asymmetric carbon atoms, it is possible to obtain as pure isomers, for example, pure enantiomers and/or pure diastereoisomers, such as pure cis/transisomers. Correspondingly, isomeric mixtures may be in the form of, for example, enantiomeric mixtures, such as racemates, diastereoisomeric mixtures or mixtures of racemates.

Resulting diastereoisomeric mixtures and mixtures of racemates can be separated into their components on the basis of the differing physical properties of the components by customary physical separating methods, for example by distillation, fractional crystallisation and/or chromatography.

Resulting enantiomeric mixtures, for example racemates, can be resolved into the enantiomers according to known methods, for example by recrystallisation from an optically active solvent, chromatography on chiral adsorbents, with the aid of suitable microorganisms, by cleavage with specific, immobilised enzymes, by means of the formation of inclusion compounds, for example using chiral Crown ethers, in which only one enantiomer is complexed, or by conversion into diastereoisomeric salts, for example by reacting a basic end product racemate with an optically active acid, such as a carboxylic acid, for example tartaric or malic acid, or a sulphonic acid, for example camphorsulphonic acid, and separating the mixture of diastereoisomers so obtained, for example on the basis of their different solubilities, into the diastereoisomers from which the desired enantiomer can then be freed by the action of suitable agents. Advantageously, the more active stereoisomer in each case is isolated.

The invention relates also to those embodiments of the process according to which a compound obtainable as an intermediate at any stage of the process is used as starting material and the remaining steps are carried out, or a starting material is used in the form of a derivative or salt and/or in the form of its racemates or enantiomers, or, especially, is formed under the reaction conditions.

The invention relates also to novel starting materials that have been developed specifically for the manufacture of the compounds obtainable in accordance with the process, especially to the preferably used selection of starting materials that results in the compounds of the formula I characterised as being preferred at the beginning, to the processes for their manufacture and to their use as intermediates.

The invention relates also to the use of compounds of the formula I, and, as the case may be, their tautomers and/or pharmaceutically acceptable salts, especially as pharmacological active ingredients, more especially as pharmacological active ingredients with anti-convulsive activity. They can be used, preferably in the form of pharmaceutical preparations, in a method for the prophylactic and/or therapeutic treatment of the animal or human body, especially as anti-convulsants, for example for the treatment of convulsions of various origins, for example for the treatment of epilepsy.

The invention relates also to pharmaceutical preparations that contain a compound of the formula I, or, as the case may be, a tautomer and/or pharmaceutically acceptable salt thereof, as active ingredient, and to processes for the manufacture thereof.

The pharmaceutical preparations in question are those which contain a therapeutically effective amount of the active ingredient, optionally together with inorganic or organic, solid or liquid pharmaceutically acceptable adjuncts, and which are suitable for enteral, for example oral, or parenteral administration to warmblooded animals. For example, pharmaceutical preparations in dosage unit form are preferably used, such as dragées, tablets, capsules or suppositories, also ampoules which contain the active ingredient together with diluents, for example lactose, dextrose, saccharose, mannitol, sorbitol, cellulose and/or glycine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat, rice or arrowroot starch, gelatine, tragacanth, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, adsorbents, colourings, flavourings and/or sweeteners. The compounds of the formula I can also be used in the form of parenterally administrable preparations or in the form of infusion solutions. Such solutions are preferably isotonic aqueous solutions or suspensions, it being possible to prepare these before use, for example in the case of lyophilised preparations which contain the active ingredient on its own or together with a carrier, for example mannitol. The pharmaceutical preparations may be sterilised and/or may contain adjuncts, for example preservatives, stabilisers, wetting agents and/or emulsifiers, solubilisers, salts for regulating the osmotic pressure and/or buffers. The novel pharmaceutical preparations which, if desired, may contain other pharmacologically active substances, are prepared in a manner known per se, for example by means of conventional mixing, granulating, confectioning, dissolving or lyophilising processes, and contain from approximately 0.1% to approximately 100%, especially from approximately 1% to approximately 50%, and in the case of lyophilisates up to 100%, active ingredient.

The dosage of the active ingredient may depend upon various factors, such as the method of administration, species of warm-blooded animal, age and/or individual condition. The daily doses to be administered in the case of oral administration are normally from approximately 5 to approximately 50 mg/kg and, for warm-blooded animals weighing approximately 70 kg, are preferably from approximately 0.5 g to approximately 5.0 g, it being possible advantageously to administer several equal partial doses to achieve the daily dosage.

The following Examples serve to illustrate the invention; they are not intended, however, to limit the scope thereof in any way. Temperatures are given in degrees Celsius.

EXAMPLE 1

320 mg (1.5 mmol) of 1-ethoxy-2-(2,6-di-fluorophenyl)-1-(N-methylimino)-ethane and 155 mg (1.5 mmol) of oxalic acid monoamide monohydrazide are dissolved under a nitrogen atmosphere in 5 ml of N-methylmorpholine and the whole is heated under reflux for 41 hours After cooling, the reaction mixture is diluted with 20 ml of dichloromethane and extracted by shaking in succession twice with water, twice with 2N hydrochloric acid and again with water. The last three acidic aqueous phases obtained are combined, rendered alkaline with concentrated ammonia solution and extracted three times with dichloromethane. The combined organic phases are dried over magnesium sulphate and concentrated. Recrystallisation of the crude product from ethanol yields 102 mg (27% of the theoretical yield) of the desired 5-(2,6-difluorobenzyl)-4-methyl-4H-1,2,4-triazole-3-carboxamide which melts at 189-190°.

The 1-ethoxy-2-(2,6-difluorophenyl)-1-(N-methylimino)-ethane can be manufactured, for example, in the following manner:

75.3 g (0.44 mol) of 2,6-difluorophenylacetic acid are dissolved in 96 ml (156.5 g; 1.32 mol) of thionyl chloride, stirred for 1 hour at 60° and then heated under reflux for 2 hours. The excess thionyl chloride is then distilled off and the residue is fractionated, yielding 79.5 g (95% of the theoretical yield) of 2,6-difluorophenylacetyl chloride.

25 ml of methylamine solution (33% in ethanol) are diluted with 90 ml of dichloromethane. While cooling, 9.52 g (50 mmol) of 2,6-difluorophenylacetyl chloride dissolved in 10 ml of dichloromethane are added dropwise in such a manner that the temperature of the reaction mixture does not exceed 10°. The reaction mixture is stirred for a further hour at 10° and then extracted three times with water. The organic phase is dried over magnesium sulphate and concentrated. The crude product is recrystallised from dichloromethane/petroleum ether and yields 8.57 g (92.6% of the theoretical yield) of 2,6-difluorophenylacetic acid methylamide of m.p. 163–164°.

5.55 g (30 mmol) of 2,6-difluorophenylacetic acid methylamide are dissolved in 70 ml of dichloromethane, 7.4 g (39 mmol) of triethyloxonium tetrafluoroborate are added thereto and the whole is stirred for 25 hours at room temperature. The reaction mixture is then extracted by shaking in succession with cold 2N sodium carbonate solution, ice-water and cold saturated sodium chloride solution, dried over magnesium sulphate and concentrated. A mixture of ether and hexane is added to the residue, the unreacted educt remaining undissolved and being filtered off. The filtrate is concentrated and subjected to distillation in a bulb tube. 4 g (62.6% of the theoretical yield) of 1-ethoxy-2-(2,6-difluorophenyl)-1-(N-methylimino)-ethane which boils at 70° (0.02 mm) are obtained.

EXAMPLE 2

The reaction of 320 mg (1.5 mmol) of 1-ethoxy-2-(2,6-difluorophenyl)-1-(N-methylimino)-ethane and 155 mg (1.5 mmol) of oxalic acid monoamide monohydrazide can be carried out, in a manner analogous to that described in Example 1, but using 5 ml of N,N-dimethylformamide as solvent. 102 mg (27% of the theoretical yield) of 5-(2,6-difluorobenzyl)-4-methyl-4H-1,2,4-triazole-3-carboxamide of m.p. 186–189° are likewise obtained.

EXAMPLE 3

5-(o-chlorobenzyl)-4-methyl-4H-1,2,4-triazole-3-carboxamide, which melts at 187–187.5° (from ethanol), can also be manufactured in a manner analogous to that described in Examples 1 and 2 by reacting 1-ethoxy-2-(o-chlorophenyl)-1-(N-methylimino)-ethane [b.p. 90° (0.02 mm)] with oxalic acid monoamide monohydrazide.

EXAMPLE 4

A mixture of 1.85 g (14 mmol) of oxalic acid monoethylamide monohydrazide and 3 g (14 mmol) of 1-ethoxy-2-(2,6-difluorophenyl)-1-(N-methylimino)-ethane is heated, while stirring, at 200° (bath temperature) for 45 minutes. After cooling, the reaction mixture is dissolved in dichloromethane. The reaction mixture is extracted by shaking in succession once with semi-concentrated hydrochloric acid (1 part concentrated hydrochloric acid/1 part water) and twice with 2N hydrochloric acid. The combined aqueous phases are extracted twice with dichloromethane, activated carbon is added thereto and the whole is filtered over Hyflo. The filtrate is rendered alkaline with concentrated ammonia solution and extracted three times with dichloromethane. The combined organic phases are washed twice with water, dried over magnesium sulphate, concentrated and crystallised from dichloromethane/-ether. Recrystallisation from ethyl acetate/ether yields 5-(2,6-difluorobenzyl)-4-methyl-4H-1,2,4-triazole-3-(N-ethyl)-carboxamide of m.p. 144–145°.

The oxalic acid monoethylamide monohydrazide can be manufactured, for example, in the following manner:

7.25 g (50 mmol) of oxalic acid monoethylamide monoethyl ester are dissolved in 70 ml of ethanol. While cooling, 2.5 ml (2.6 g; 52 mmol) of hydrazine hydrate dissolved in 10 ml of ethanol are added dropwise in such a manner that the temperature of the reaction mixture does not exceed 10°. The reaction mixture is then stirred for one hour at room temperature and the oxalic acid monoethylamide monohydrazide, m.p. 161–164°, which has precipitated is filtered off.

EXAMPLE 5

10 g (36 mmol) of 5-(2,6-difluorobenzyl)- 4-methyl-4H-1,2,4-triazole-3-carboxylic acid ethyl ester are stirred in 100 ml of 4.4N ammoniacal ethanol for 2 hours at 70° in a bomb tube. The reaction mixture is then concentrated to half its volume. The resulting crystals are filtered off, recrystallised from ethanol and yield 5-(2,6-difluorobenzyl)-4-methyl-4H-1,2,4-triazole-3-carboxamide of m.p. 189–191°.

The 5-(2,6-difluorobenzyl)-4-methyl-4H-1,2,4-triazole-3-carboxylic acid ethyl ester can be manufactured, for example, in the following manner:

70.4 g (0.41 mol) of 2,6-difluorophenylacetic acid, 700 ml of ethanol and 35 ml of concentrated sulphuric acid are heated under reflux for 3 hours. The reaction mixture is then concentrated by evaporation, taken up in dichloromethane and the solution is extracted by shaking in succession with water, 2N sodium carbonate solution and again with water. After drying over magnesium sulphate, the organic phase is concentrated by evaporation. The residue is dissolved in 560 ml of ethanol. After the addition of 30 ml (31 g; 0.62 mol) of hydrazine hydrate, the whole is heated under reflux for 4 days. After cooling, the resulting crystals are filtered off to yield 56.4 g (74% of the theoretical yield) of 2,6-difluorophenylacetic acid hydrazide which melts at 177–178°.

18.6 g (142 mmol) of oxalic acid monomethylamide monoethyl ester are dissolved under a nitrogen atmosphere in 63 ml of trichloromethane, and 59 ml of a 20% solution of phosgene in toluene are added thereto. At a temperature of 5–10°, 9.2 ml of pyridine are added dropwise. The reaction mixture is then stirred for 2 hours at 0°, nitrogen being blown through the reaction mixture during the second hour. 17.6 g (95 mmol) of 2,6-difluorophenylacetic acid hydrazide are then added The reaction mixture is subsequently stirred for 40 minutes at room temperature, then poured onto ice-water, acidified with concentrated hydrochloric acid and extracted three times with ether. The acidic aqueous phase is rendered alkaline with concentrated ammonia solution and extracted by shaking three times with dichloromethane. The combined dichloromethane phases are washed twice with water, dried over magnesium sulphate and concentrated by evaporation. The residue is taken up in 160 ml of xylene and stirred under reflux for 9 hours. The reaction mixture is then concentrated and chromatographed over silica gel using ethyl acetate as eluant. The eluate is concentrated by evaporation and the crystalline residue is recrystallised from ethyl acetate/ether. 5-(2,6-difluorobenzyl)-4-methyl-4H-1,2,4-triazole-3-carboxylic acid ethyl ester of m.p. 127–128° is obtained.

EXAMPLE 6

The following can be manufactured in a manner analogous to that described in Example 5:
from o-fluorophenylacetic acid hydrazide (m.p. 139–143°), phosgene and oxalic acid monomethylamide monoethyl ester, 5-(o-fluorobenzyl)-4-methyl-4H-1,2,4-triazole-3-carboxylic acid ethyl ester (m.p. 83–84°) and, from the latter, 5-(o-fluorobenzyl)-4-methyl-4H-1,2,4-triazole-3-carboxamide of m.p. 165–166° and
from m-trifluoromethylphenylacetic acid hydrazide (m.p. 102–104°), phosgene and oxalic acid monomethylamide monoethyl ester, 4-methyl-5-(m-trifluoromethylbenzyl)-4H-1,2,4-triazole-3-carboxylic acid ethyl ester (m.p. 64–65°) and, from the latter, 4-methyl-5-(m-trifluoromethylbenzyl)-4H-1,2,4-triazole-3-carboxamide of m.p. 167–168°.

EXAMPLE 7

In a manner analogous to that described in Example 5 it is possible to manufacture from 2,6-difluorophenylacetic acid hydrazide (m.p. 177–178°), phosgene and oxalic acid monoethylamide monoethyl ester, 4-ethyl-5-(2,6-difluorobenzyl)-4H-1,2,4-triazole-3-carboxylic acid ethyl ester (m.p. 120–121°) and, from the latter, 4-ethyl-5-(2,6-di-fluorobenzyl)-4H-1,2,4-triazole-3-carboxamide of m.p. 222–224°.

EXAMPLE 8

In a manner analogous to that described in Example 5 it is possible to manufacture from 5-(2,6-difluorobenzyl)-4-methyl-4H-1,2,4-triazole-3-carboxylic acid ethyl ester (m.p. 127–128°) also
using methylamine instead of ammonia, 5-(2,6-difluorobenzyl)-4-methyl-4H-1,2,4-triazole-3-(N-methyl)carboxamide of m.p. 179–180° and,
using dimethylamine instead of ammonia, 5-(2,6-difluorobenzyl)-4-methyl-4H-1,2,4-triazole-3-(N,N-dimethyl)-carboxamide of m.p. 124–126°.

EXAMPLE 9

In a manner analogous to that described in benzyl)-4-methyl-4H-1,2,4-triazole-3-carboxylic acid thyl ester, 5-(o-chlorobenzyl)-4-methyl-4H-1,2,4-triazole-3-carboxamide of m.p. 187–187.5°.

The 5-(o-chlorobenzyl)-4-methyl-4H-1,2,4-triazole-3-carboxylic acid ethyl ester can be manufactured, for example, in the following manner:

14.8 g (80 mmol) of o-chlorophenylacetic acid hydrazide are suspended in 230 ml of dichloromethane. At 5°, 12 g (80 mmol) of 2-chloro-2-(N-methylimino)-acetic acid ethyl ester [Tetrahedron Lett. 30, 2827 (1979)] are added dropwise thereto. The whole is then stirred for 2 hours while cooling with ice and then overnight at room temperature. The reaction mixture is then poured onto ice, 50 ml of 2N hydrochloric acid are added thereto and the whole is extracted twice with dichloromethane. The combined dichloromethane phases are washed twice with water. All the acidic aqueous phases are combined, rendered alkaline with solid sodium carbonate and extracted three times by shaking with dichloromethane. These three organic phases are combined, washed in succession with water and saturated sodium chloride solution, dried over magnesium sulphate and concentrated by evaporation. The residue is taken up in 150 ml of xylene and stirred under reflux for 44 hours. The reaction mixture is then concentrated and chromatographed over silica gel using ethyl acetate as eluant. The eluate is concentrated by evaporation and recrystallised from ether. 5-(o-chlorobenzyl)-4-methyl-4H-1,2,4-triazole-3-carboxylic acid ethyl ester of m.p. 87–88° is obtained in a yield of 12.4 g (55% of the theoretical yield).

EXAMPLE 10

1.43 g (6 mmol) of 5-(2,6-difluorobenzyl)-3-hydroxymethyl-4-methyl-4H-1,2,4-triazole and 5.22 g (60 mmol) of manganese dioxide are heated under reflux in 40 ml of toluene for 3 hours using a water separator. The reaction mixture is then cooled and filtered over Hyflo, and the filtrate is concentrated by evaporation. The residue is added to 90 ml of isopropanol saturated with ammonia. At 0°, 1 47 g (30 mmol) of sodium cyanide and 10.44 g (120 mmol) of manganese dioxide are added. The reaction mixture is stirred for 4 hours at 0° and filtered over Hyflo. The filtrate is concentrated by evaporation. Recrystallisation of the residue from ethanol yields the pure 5-(2,6-difluorobenzyl)-4-methyl-4H-1,2,4-triazole-3-carboxamide The 5-(2,6-difluorobenzyl)-3-hydroxymethyl-4-methyl- 4H-1,2,4-triazole can be manufactured, for example, in a manner analogous to that described in Example 1 or 4 by reacting 2.13 g (10 mmol) of 1-ethoxy-2-(2,6-difluorophenyl)-1-(N-methylimino)-ethane with 0.9 g (10 mmol) of hydroxyacetic acid hydrazide.

EXAMPLE 11

70.7 g (300 mmol) of 1-ethoxy-2-(2,6-difluorophenyl)-1-imino-ethane hydrochloride are added, while stirring, to a suspension of 30.9 g (300 mmol) of oxalic acid monoamide monohydrazide in 900 ml of N,N-dimethylformamide. The reaction mixture is heated to 80° and stirred at this temperature for 1 hour. During a period of 20 minutes 10.6 g of methylamine are passed into the resulting white suspension, which leads to the formation of a clear yellow solution. During a period of 1 hour a further 15.9 g of methylamine are passed into the solution. The solution is then stirred for another hour at 80°. The solvent is evaporated in vacuo. 400 ml of water are added to the residue. The aqueous mixture is stirred and the crystals are filtered off. 300 ml of water are added to the crystals. The mixture is again stirred and the crystals are filtered off. The crystals are dissolved in hot ethanol (ca. 500 ml). After the addition of activated charcoal the mixture is filtered over Hyflo. The filtrate is evaporated until crystallisation starts (ca. 230 ml of ethanol have to be distilled off). The mixture is then cooled in an ice bath. The crystals are filtered off and dried overnight in vacuo, yielding the product of example 1.

The 1-ethoxy-2-(2,6-difluorophenyl)-1-imino-ethane hydrochloride can be obtained, for example, as follows: 153 g (1 mol) of 2-(2,6-difluorophenyl)acetonitrile are dissolved in a mixture of 116 ml (2 mol) of ethanol and 00 ml of diethyl ether. The solution is cooled to from +5° to 10° . At this temperature 73 g (2 mol) of hydrogen chloride are passed into the solution. The mixture is then left to stand for 2 days at +5°. The resulting crystals are filtered off and washed with diethylether. After recrystallisation from ethanol/diethyl ether the crystals are dried overnight in vacuo, yielding the desired starting material.

EXAMPLE 12

The following compounds can also be manufactured in a manner analogous to that described in Examples 1 to 11:

5-(o-chlorobenzyl)-1,2,4-triazole-3-carboxamide, m.p. 208–214°,
5-(2,6-difluorobenzyl)-1,2,4-triazole-3-carboxymide, m.p. 203–204°,
5-[1-(2,6-difluorophenyl)ethyl]-4-methyl-4H-1,2,4-triazole-3-carboxamide, and
5-(2,6-difluorobenzyl)-4-methyl-4H-1,2,4-triazole-3-(N-acetyl)-carboxamide.

EXAMPLE 13

Tablets, each containing 50 mg of active ingredient, for example 5-(2,6-difluorobenzyl)-4-methyl-4H-1,2,4-triazole-3-carboxamide, can be manufactured, for example, as follows:

Composition (for 10,000 tablets)

| Composition (for 10,000 tablets): | |
| --- | --- |
| active ingredient | 500.0 g |
| lactose | 500.0 g |
| potato starch | 352.0 g |
| gelatine | 8.0 g |
| talc | 60.0 g |
| magnesium stearate | 10.0 g |
| silica (highly dispersed) | 20.0 g |
| ethanol | q.s. |

The active ingredient is mixed with the lactose and 292 g of potato starch, and the mixture is moistened with an alcoholic solution of the gelatine and granulated through a sieve. After drying, the remainder of the potato starch, the talc, magnesium stearate and the highly dispersed silica are admixed and the mixture is compressed to form tablets each weighing 145.0 mg and containing 50.0 mg of active ingredient, which, if desired, may be provided with dividing notches for finer adjustment of the dosage.

EXAMPLE 14

Lacquer-coated tablets, each containing 100 mg of active ingredient, for example 5-(2,6-difluorobenzyl)-4-methyl-4H-1,2,4-triazole-3-carboxamide, can be manufactured, for example, as follows:

Composition (for 1000 tablets)

| Composition (for 1000 tablets): | |
| --- | --- |
| active ingredient | 100.00 g |
| lactose | 100.00 g |
| corn starch | 70.00 g |
| talc | 8.50 g |
| calcium stearate | 1.50 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed, moistened with a paste prepared from 15 g of corn starch and water (while heating) and granulated. The granulate is dried, and the remainder of the corn starch, the talc and the calcium stearate are added and mixed with the granulate. The mixture is compressed to form tablets (weight 280 mg) and these are coated with a solution of the hydroxypropylmethylcellulose and the shellac in dichloromethane; final weight of a lacquer-coated tablet 283 mg.

EXAMPLE 15

In a manner analogous to that described in Examples 13 and 14 it is possible to manufacture also pharmaceutical preparations containing a different compound of the formula I or, as the case may be, a tautomer and/or a pharmaceutically acceptable salt thereof, for example in accordance with Examples 1 to 12.

I claim:
1. A compound of the formula

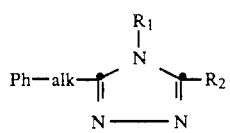

in which Ph represents phenyl substituted by lower alkyl, halogen and/or by trifluoromethyl, alk represents lower alkylidene, $R_1$ is hydrogen or lower alkyl, and $R_2$ represents carbamoyl that is unsubstituted or is substituted by lower alkyl or by lower alkanoyl, with the proviso that, in a compound of the formula I in which $R_1$ represents methyl, $R_2$ represents N,N-diethylcarbamoyl and alk represents methylene, Ph is other than phenyl substituted in the p-position by chlorine, or, as the case may be, a tautomer thereof, in each case in free form or in form of a pharmaceutically acceptable salt.

2. A compound of the formula I according to claim 1, in which Ph represents phenyl mono-, di- or tri-substituted by lower alkyl, halogen and/or by trifluoromethyl, alk represents lower alkylidene, $R_1$ is hydrogen or lower alkyl, and $R_2$ represents carbamoyl, N-lower alkylcarbamoyl, N,N-di-lower alkylcarbamoyl or N-lower alkanoylcarbamoyl, or, as the case may be, a tautomer thereof, in each case in free form or in form of a pharmaceutically acceptable salt.

3. A compound of the formula I according to claim 1, in which Ph represents phenyl mono-substituted by $C_1$–$C_4$-alkyl, halogen or by trifluoromethyl or di-substituted by halogen, by halogen and $C_1$–$C_4$-alkyl, or by halogen and trifluoromethyl, wherein halogen in each case has an atomic number of up to and including 35, alk represents 1,1- or 2,2-$C_1$–$C_4$-alkylidene, $R_1$ is hydrogen or $C_1$–$C_4$-alkyl, and $R_2$ represents carbamoyl, N-$C_1$–$C_4$-alkylcarbamoyl, N,N-di-$C_1$–$C_4$-alkylcarbamoyl or N-$C_2$–$C_7$-alkanoylcarbamoyl, or, as the case may be, a tautomer thereof, in each case in free form or in form of a pharmaceutically acceptable salt.

4. A compound of the formula I according to claim 1, in which Ph carries at least one of the lower alkyl and/or halogen substituents in an o-position or a trifluoromethyl substituent in a m-position, or, as the case may be, a tautomer thereof, in each case in free form or in form of a pharmaceutically acceptable salt.

5. A compound of the formula I according to claim 1, in which Ph represents o-$C_1$–$C_4$-alkylphenyl, m-trifluoromethylphenyl, o-halophenyl or 2,3-, 2,4-, 2,5- or 2,6-dihalophenyl, wherein halogen in each case has an atomic number of up to and including 35, alk represents 1,1-$C_1$–$C_4$-alkylidene, $R_1$ is hydrogen or $C_1$–$C_4$-alkyl, and $R_2$ represents carbamoyl or N-$C_1$–$C_4$-alkylcarbamoyl, N,N-di-$C_1$–$C_4$-alkylcarbamoyl or N-$C_2$–$C_7$-alkanoylcarbamoyl, or, as the case may be, a tautomer thereof, in each case in free form or in form of a pharmaceutically acceptable salt.

6. A compound of the formula I according to claim 1 with the further proviso that Ph is other than phenyl mono-substituted by halogen, especially by chlorine, when $R_2$ represents N,N-di-$C_1$–$C_4$-alkylcarbamoyl in which the two N-alkyl groups are identical or different, or, as the case may be, a tautomer thereof, in each case in free form or in form of a pharmaceutically acceptable salt.

7. A compound of the formula I according to claim 1, in which Ph represents m-tri-fluoromethylphenyl, o-fluorophenyl or 2,6-difluorophenyl, alk represents methylene, $R_1$ is $C_1$–$C_4$-alkyl, and $R_2$ represents carbamoyl, in each case in free form or in form of a pharmaceutically acceptable salt.

8. A compound of the formula I according to claim 1, in which Ph represents m-trifluoromethylphenyl or 2,6-difluorophenyl, alk represents methylene, $R_1$ is $C_1$–$C_4$-alkyl, and $R_2$ represents carbamoyl, in each case in free form or in form of a pharmaceutically acceptable salt.

9. A compound according to claim 1 being 5-(2,6-difluorobenzyl)-4-methyl-4H-1,2,4-triazole-3-carboxamide or a pharmaceutically acceptable salt thereof.

10. A compound according to claim 1 being 5-(o-chlorobenzyl)-4-methyl-4H-1,2,4-triazole-3-carboxamide or a pharmaceutically acceptable salt thereof.

11. A compound according to claim 1 being 5-(o-fluorobenzyl)-4-methyl-4H-1,2,4-triazole-3-carboxamide or a pharmaceutically acceptable salt thereof.

12. A compound according to claim 1 being 4-methyl-5-(m-trifluoromethylbenzyl)-4H-1,2,4-triazole-3-carboxamide or a pharmaceutically acceptable salt thereof.

13. A compound according to claim 1 being 4-ethyl-5-(2,6-difluorobenzyl)-4H-1,2,4-triazole-3-carboxamide or a pharmaceutically acceptable salt thereof.

14. A compound according to claim 1 being 5-(2,6-difluorobenzyl)-4-methyl-4H-1,2,4-triazole-3-(N-methyl)carboxamide or a pharmaceutically acceptable salt thereof.

15. A compound according to claim 1 being 5-[1-(2,6-difluorophenyl)ethyl]-4-methyl-4H-1,2,4-triazole-3-carboxamide or a pharmaceutically acceptable salt thereof.

16. A compound according to claim 1 being 5-(2,6-difluorobenzyl)-4-methyl-4H-1,2,4-triazole-3-(N-acetyl)carboxamide or a pharmaceutically acceptable salt thereof.

17. A pharmaceutical preparation containing an anticonvulsively effective amount of a compound of the formula

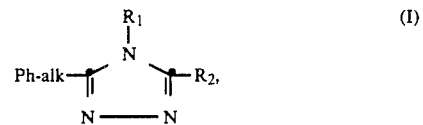

in which Ph represents phenyl substituted by lower alkyl, halogen and/or by trifluoromethyl, alk represents lower alkylidene, $R_1$ is hydrogen or lower alkyl, and $R_2$ represents carbamoyl that is unsubstituted or is substituted by lower alkyl or by lower alkanoyl, or, as the case may be, a tautomer thereof, in each case in free form or in form of a pharmaceutically acceptable salt, optionally together with customary pharmaceutical adjuncts.

18. A pharmaceutical preparation containing an anticonvulsively effective amount of a compound according to claim 1, or, as the case may be, a tautomer thereof, in each case in free form or in form of a pharmaceutically acceptable salt, optionally together with customary pharmaceutical adjuncts.

19. A compound according to claim 1 being 5-(2,6-difluorobenzyl)-1,2,4-triazole-3-carboxamide or a pharmaceutically acceptable salt thereof.

* * * * *